US006607717B1

(12) United States Patent
Johnson et al.

(10) Patent No.: US 6,607,717 B1
(45) Date of Patent: Aug. 19, 2003

(54) SILICON BASED QUATERNARY AMMONIUM FUNCTIONAL COMPOSITIONS AND THEIR APPLICATIONS

(75) Inventors: Bethany K. Johnson, Midland, MI (US); John Joseph Kennan, Midland, MI (US); Feifei Lin, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/001,753

(22) Filed: Oct. 24, 2001

(51) Int. Cl.$^7$ .............................. A61K 7/075; A61K 7/08
(52) U.S. Cl. ................ 424/70.12; 424/70.1; 424/70.19; 424/70.27; 424/70.2; 424/401; 514/937
(58) Field of Search .............................. 424/70.1, 70.12, 424/70.27, 70.19, 401, 70.2; 514/937

(56) References Cited

U.S. PATENT DOCUMENTS

| 3,389,160 A | 6/1968 | Reid ........................ 260/448.2 |
| 4,118,316 A | 10/1978 | Talley et al. ............... 210/31 C |
| 4,818,242 A | 4/1989 | Burmeister et al. |
| 4,891,166 A | 1/1990 | Schaefer et al. .......... 260/404.5 |
| 4,895,964 A | 1/1990 | Margida ..................... 556/425 |
| 5,098,979 A | 3/1992 | O'Lenick, Jr. ................ 528/15 |
| 5,164,522 A | 11/1992 | McCarthy et al. ............. 554/39 |
| 6,245,924 B1 | 6/2001 | Imperante .................... 556/405 |
| 6,482,969 B1 * | 11/2002 | Helmrick et al. ............ 556/420 |

FOREIGN PATENT DOCUMENTS

| FR | 1589218 | 4/1970 |
| JP | 54087709 A | 7/1979 |
| JP | 7070204 A | 3/1995 |
| JP | 2002308991 A | 10/2002 |
| WO | WO 99/62957 | 12/1999 |
| WO | WO 01/41721 A1 | 6/2001 |

OTHER PUBLICATIONS

WO 01/41721, Abstract (6/01).*
JP 54087709, Abstract (7/79).*
FR 1589218, Abstract (4/70).*
JP 707024, Abstract (3/95).*
JP 61034004, Abstract (2/86).*
DE 3301667, Abstract (7/84).*

* cited by examiner

*Primary Examiner*—Jyothsan Venkat
(74) *Attorney, Agent, or Firm*—Charles R. Richard; Jim L. DeCesare; Alan Zombeck

(57) ABSTRACT

There are disclosed novel quaternary ammonium functional silicone based emulsions and other formulations, as well as methods to make such emulsions and formulations. These materials have uses in personal care and other applications.

9 Claims, No Drawings

SILICON BASED QUATERNARY AMMONIUM FUNCTIONAL COMPOSITIONS AND THEIR APPLICATIONS

FIELD OF THE INVENTION

This invention relates to silicon based quaternary ammonium functional compositions and to their applications. More particularly, the invention relates to novel emulsions and other formulations containing quaternary ammonium functional silicones, methods of making these emulsions and other formulations, and their uses.

BACKGROUND OF THE INVENTION

Because of their positive charge, quaternary ammonium functional silicones are useful in treating materials and surfaces that are primarily negatively charged, such as in many textile and personal care applications. The quaternary ammonium functionality makes possible certain ionic interactions that are the basis of many useful properties. These include increased hydrophilic character, ability to act as a thickener, and improved ability to aid in the deposition of other materials such as coatings and conditioning agents.

Some quaternary ammonium functional silicones and methods for making them are known in the art. For example, Reid in U.S. Pat. No. 3,389,160 discloses a group of these materials and a two step method for making them. In the first step, an epoxy functional silicone is reacted with a secondary amine to form a tertiary amine functional silicone. The product is reacted with an alkyl halide to yield a quaternary ammonium functional silicone in the second step.

Margida in U.S. Pat. No. 4,895,964 discloses certain pendant quaternary ammonium functional silicones and a one step method for making them. Here, a tertiary amine salt is reacted with a pendant epoxy functional silicone. A group of terminal quaternary ammonium functional silicones is disclosed by Schaefer et al. in U.S. Pat. No. 4,891,166, as well as a method for making them. This method is similar to the method in Margida, except that a terminal epoxy functional silicone is used.

McCarthy et al. in U.S. Pat. No. 5,164,522 discloses a class of quaternary ammonium functional silicones and a method for making them; the method involves treating diamine functional silicones with ethylene oxide followed by reaction with dimethyl sulfate. In U.S. Pat. No. 5,098,979 to O'Lenick, another group of quaternary ammonium functional silicones is disclosed along with a two step method for making them. This method involves reacting a silicone polyether having a terminal —OH group with epichlorohydrin (an epoxide), and the resulting product is reacted with a tertiary amine.

Most recently, new quaternary ammonium functional silicones and methods for making them are disclosed in a companion U.S. patent application to the present case, filed the same day, invented by Helmrick and Kennan, and entitled, "Silicon Based Quaternary Ammonium Functional Compositions and Methods For Making Them", which is hereby incorporated by reference. Some of these silicones have been found to perform especially well in a number of personal care applications and are described below. The present invention concerns emulsions and other formulations of these silicones, methods of making these materials and their uses.

SUMMARY OF THE INVENTION

It is an object of this invention to provide novel quaternary ammonium functional silicon based compositions. Thus, this invention relates to a quaternary ammonium functional silicone ("silicone quat") based composition comprising:

(A) a Kennan silicone quat (as defined herein below);
(B) a surface active agent; and
(C) water.

A further object of this invention is to provide methods to make silicone based quaternary ammonium functional compositions and more particularly emulsions. Thus, this invention relates to a method for making a quaternary ammonium functional silicone based composition, the method comprising:

combining at least one member of the group consisting of
  Kennan silicone quat based emulsions;
  Kennan silicone quats diluted in
    hydrocarbons, alcohols, silicones other than quaternary ammonium functional silicones or mixtures thereof;
  Kennan silicone quats; and
  mixtures thereof
  with at least one member of the group consisting of a Kennan silicone quat, a surface active agent and water.

The invention also relates to a method for making a quaternary ammonium functional silicone based emulsion, the method comprising:

(1) mixing a Kennan silicone quat and at least one surface active agent optionally diluted with water; and
(2) combining water and at least a portion of the mixture from (1) if water is not already present therein.

In addition, the invention further relates to silicone quaternary ammonium functional compositions expressed in terms of the methods used to make them:

the composition produced by the method comprising combining at least a Kennan silicone quat, a surface active agent and water; and the composition produced by the method comprising emulsifying a Kennan silicone quat with at least a surface active agent and water.

DETAILED DESCRIPTION OF THE INVENTION

The compositions according to the present invention are based on members of a class of silicon based quaternary ammonium functional materials first disclosed in the companion to this case identified previously. This class can be described as follows.

A silicon based quaternary ammonium functional composition comprising the group, $-R^1-Z-Q^3$, where, $-R^1-$ is either a divalent hydrocarbon group, which may optionally incorporate ether or ester functionality, or $-R^{17}N(Q^1)R^{18}-$, and is covalently bonded to Si in an unsupported (free, not covalently bonded to a support such as a glass bead) silicone or silane;

$-Z-$ is $-C(O)O-$ or $-N(Q^2)-$;

$-Q^3$ is $-CH(R^3)CH(OH)YN^+(R^4)(R^5)(R^6)$ $X^-$, hydrogen or a monovalent hydrocarbon group that may optionally incorporate hydroxy, diol, amide, ether or ester functionality;

$-R^{17}-$ and $-R^{18}-$ are independently divalent hydrocarbon groups that may optionally incorporate ether or ester functionality;

$-Q^1$ and $-Q^2$ are independently

—CH($R^3$)CH(OH)Y$N^+$($R^4$)($R^5$)($R^6$)$X^-$, hydrogen or a monovalent hydrocarbon group that may optionally incorporate hydroxy, diol, amide, ether or ester functionality;

Y is a divalent hydrocarbon group;

$R^3$ is a monovalent hydrocarbon group or hydrogen;

$R^4$, $R^5$ and $R^6$ are independently monovalent hydrocarbon groups; and $X^-$ is a counter ion, with the proviso that at least one of —$Q^1$, —$Q^2$ and —$Q^3$ is —CH($R^3$)CH(OH)Y$N^+$($R^4$)($R^5$)($R^6$) $X^-$.

Members of this class of silicon based materials that are of special interest in relation to the present invention are those comprising an —$R^1$— covalently bonded to Si in an unsupported silicone. In this disclosure and the claims that follow, this group of materials of special interest will be designated as "Kennan silicone quats".

In this disclosure and the claims that follow, a subset of the Kennan silicone quats, to be designated as "type I Kennan silicone quats" (the type I embodiment in the companion case previously identified), is defined as follows.

A silicone composition having an average formula (based on the silicone molecules and their number present in a given sample):

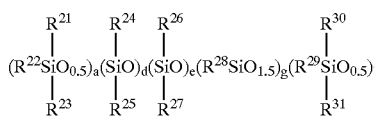

where $R^{21}$, $R^{22}$, $R^{23}$, $R^{30}$ and $R^{31}$ are independently hydroxy, phenoxy, alkoxy or monovalent hydrocarbon groups;

$R^{24}$, $R^{25}$ and $R^{27}$ are independently monovalent hydrocarbon groups;

$R^{28}$ is a monovalent hydrocarbon group, or contains nitrogen and may at least in part represent a group or groups of the form —$R^1$—Z—$Q^3$;

$R^{26}$ and $R^{29}$ contain nitrogen and where present represent, at least in part, a group or groups of the form —$R^1$—Z—$Q^3$;

—$R^1$— is either a divalent hydrocarbon group, that may optionally incorporate ether or ester functionality, or —$R^{17}$N($Q^1$)$R^{18}$—;

—$R^{17}$— and —$R^{18}$— are independently divalent hydrocarbon groups that may optionally incorporate ether or ester functionality;

—$Q^1$ is —CH$_2$CH(OH)CH$_2$N$^+$($R^4$)($R^5$)($R^6$) $X^-$, hydrogen or a monovalent hydrocarbon group that may optionally incorporate hydroxy, diol, amide, ether or ester functionality;

$R^4$, $R^5$ and $R^6$ are independently monovalent hydrocarbon groups;

$X^-$ is a counter ion;

—Z— is —N($Q^2$)—;

—$Q^3$ and —Q2 are independently —CH$_2$CH(OH)CH$_2$N$^+$ ($R^4$)($R^5$)($R^6$) $X^-$, hydrogen or a monovalent hydrocarbon group that may optionally incorporate hydroxy, diol, amide, ether or ester functionality;

a, b, d, e and g are all greater than or equal to zero;

a=0 to 2+g;

b=0 to 2+g;

d=0 to 500;

e=0 to 100;

g=0 to 100;

a+b is greater than or equal to 2; and e+b>0, with the proviso that at least a portion of $Q^1$, $Q^2$, and $Q^3$ present in the composition is —CH$_2$CH(OH)CH$_2$N$^+$($R^4$) ($R^5$)($R^6$) $X^-$.

The depiction of the average formula defining type I Kennan silicone quats should not be regarded as completely structural nor should it be regarded as defining any specific stereospecificity. The formula should be regarded as semi-empirical. For example, where d=3, the formula would represent a material having on average 3 of the units corresponding to the d subscript per molecule, but these subunits could be located anywhere on the chain (except at the endpoints in this case), and not necessarily contiguous.

One subset of type I Kennan silicone quats of interest, designated here as "type II Kennan silicone quats" (the "type II embodiment" in the companion case previously mentioned), is defined as follows. (Note that the expressions, "up to 20 carbons", and "1 to 20 carbons" have the same meaning in the context of monovalent hydrocarbon groups and the like.)

A type I Kennan silicone quat, wherein:

$R^{21}$, $R^{22}$, $R^{23}$, $R^{30}$ and $R^{31}$ are independently hydroxy, or alkoxy or monovalent hydrocarbon groups having 1 to 20 carbons;

$R^{24}$, $R^{25}$ and $R^{27}$ are independently monovalent hydrocarbon groups having 1 to 20 carbons;

$R^{28}$ is a monovalent hydrocarbon group having 1 to 20 carbons, or contains nitrogen and may at least in part represent a group or groups of the form —$R^1$—Z—$Q^3$;

—$R^1$— is either a divalent hydrocarbon group having 1 to 20 carbons, that may optionally incorporate ether or ester functionality, or —$R^{17}$N($Q^1$)$R^{18}$—;

—$R^{17}$— and —$R^{18}$— are independently divalent hydrocarbon groups having 1 to 20 carbons that may optionally incorporate ether or ester functionality;

—$Q^1$ is —CH$_2$CH(OH)CH$_2$N$^+$($R^4$)($R^5$)($R^6$) $X^-$, hydrogen or a monovalent hydrocarbon group having 1 to 20 carbons that may optionally incorporate hydroxy, diol, amide, ether or ester functionality;

$R^4$, $R^5$ and $R^6$ are independently monovalent hydrocarbon groups having 1 to 20 carbons;

$X^-$ is a counter ion;

—$Q^3$ and —$Q^2$ are independently —CH$_2$CH(OH)CH$_2$N$^+$ ($R^4$)($R^5$)($R^6$) $X^-$, hydrogen or a monovalent hydrocarbon group having 1 to 20 carbons that may optionally incorporate hydroxy, diol, amide, ether or ester functionality;

d=0 to 400;

e=0 to 50;

g=0 to 50; and (e+b)/(a+b+d+e+g)=0.005 to 0.05;

with the proviso that 10 to 75 percent of $Q^1$, $Q^2$, and $Q^3$ present in the composition (the percentage based on the total number of these groups) is —CH$_2$CH(OH)CH$_2$N$^+$($R^4$)($R^5$) ($R^6$) $X^-$.

Another subset of type I Kennan silicone quats of interest (also a subset of type II Kennan silicone quats), designated "type III Kennan silicone quats" here (the "type III embodiment" in the companion case previously mentioned), is defined as follows.

A type I Kennan silicone quat, wherein:

$R^{21}$, $R^{22}$, $R^{23}$, $R^{30}$ and $R^{31}$ are independently hydroxy, methoxy or methyl groups;

$R^{24}$ $R^{25}$ and $R^{27}$ are methyl groups;

$R^{28}$ is a methyl group, or contains nitrogen and may at least in part represent a group or groups of the form —$R^1$—Z—$Q^3$;

—$R^1$— is either a propylene group or —$R^{17}N(Q^1)R^{18}$—;

—$R^{17}$— is a propylene or an isobutylene group and —$R^{18}$— is an ethylene group;

—$Q^1$ is —$CH_2CH(OH)CH_2N^+(R^4)(R^5)(R^6)$ $X^-$, hydrogen or a methyl group;

$R^4$ and $R^5$ are methyl groups;

$R^6$ is a methyl, dodecyl or octadecyl group;

$X^-$ is a counter ion;

—$Q^3$ and —$Q^2$ are independently —$CH_2CH(OH)CH_2N^+(R^4)(R^5)(R^6)$ $X^-$, hydrogen or a methyl group;

d=50 to 150;

e=0 to 10;

g=0 to 5; and (e+b)/(a+b+d+e+g)=0.01 to 0.03, with the proviso that 25 to 40 percent of $Q^1$, $Q^2$, and $Q^3$ present in the composition (the percentage based on the total number of these groups) is —$CH_2CH(OH)CH_2N^+(R^4)(R^5)(R^6)$ $X^-$.

The Kennan silicone quats described can be made by methods disclosed in the previously defined companion case. These methods are illustrated in the examples below.

The compositions according to the present invention are quaternary ammonium functional silicone based compositions comprising:

(A) a Kennan silicone quat;

(B) a surface active agent; and (C) water.

These compositions may be used in many applications, such as personal care, including as rinse-off conditioners, leave-on conditioners, conditioners used before and after coloring or bleaching, ethnic conditioning products, conditioning shampoos, shampoos, in hair colorants, in ethnic relaxants, as body washes and moisturizers, as well as in textile care and treatment. Due to good compatibility of quaternary ammonium functional silicones with hydrocarbons, silicones and alcohols, these functional silicones may be incorporated into non-aqueous personal care products such as hair styling aids, fixatives and shine products for providing conditioning and body benefit in these product segments.

As consumers desire to spend less time on personal care without sacrificing results, there is a need for cosmetic products with multiple benefits. In the hair care industry, for example, a current major market need is conditioning plus a body benefit. In this context, conditioning may be defined as the action of a hair treatment product to improve the compatibility relative to a control or for the product to reduce the combing forces after application to the hair. Hair body may be defined as thickness or apparent volume of a hair assembly, involving sight and touch for assessment. Usually there is a trade-off between the two benefits. This effect may be due to the conditioner decreasing the interfiber friction of the hair fibers. The quaternary ammonium functional silicone based formulations of the present invention provide both an excellent conditioning effect on the hair plus the added benefit of body.

Some specific surface active agents that have been found to perform well in the compositions of the present invention, notably in conditioners, are waxes (natural, as well as synthetic, such as petroleum based), glyceryl esters (such as stearates), fatty alcohols (especially those having 10 to 18 carbons), other nonionic surfactants and mixtures of these (the mixtures being of any or all of these, of course). Other surface active agents that perform well in these compositions, notably in shampoos, include nonionic surfactants, anionic surfactants, amphoteric surfactants and mixtures of these. Further, such agents that perform well, notably in moisturizers, include waxes (natural, as well as synthetic, such as petroleum based), silicone polyoxyalkylene copolymers, other nonionic surfactants, anionic surfactants and mixtures of these.

Compositions of the present invention include those that further comprise:

(D) a conditioning agent (especially one selected from the group consisting of cationic polymers, cationic surfactants, proteins, natural oils, silicones other than quaternary ammonium functional silicones and mixtures thereof), a hydrocarbon other than a wax, an anionic surfactant, an amphoteric surfactant or a mixture thereof;

(E) a cosurfactant, especially one selected from the group consisting of betaines, monoalkyl alkanolamides, dialkyl alkanolamides, amine oxides, amine glycinates, amine propionates, amine sultaines and mixtures thereof;

(F) a conditioning agent (especially one selected from the group consisting of cationic polymers, cationic surfactants, proteins, waxes, natural oils, silicones other than quaternary ammonium functional silicones and mixtures thereof), a hydrocarbon other than a wax or a mixture thereof;

(G) a polyhydric alcohol such as glycerin or sorbitol;

(H) a material selected from the group consisting of a hydrocarbon other than a wax, a natural oil, a cationic surfactant, an amphoteric surfactant and mixtures thereof; or mixtures thereof (the mixtures thereof being of any or all of (D) through (H) that are distinct, of course).

These more specific compositions have been found to be especially useful in personal care applications. Those further comprising (D) are especially useful as conditioners, while those further comprising (E) and/or (F) are especially useful as shampoos. The ones further comprising (G) and/or (H) are especially useful as moisturizers.

Further more specific compositions of the present invention, and of special interest, include those comprising:

0.01 to 25, especially 0.1 to 2, weight percent (A);

0.1 to 25, especially 1 to 10, weight percent (B); and 0.5 to 99.89, especially 50 to 98.9, weight percent (C), as well as those further comprising up to 10 weight percent of (J), a conditioning agent selected from the group consisting of cationic polymers, cationic surfactants, proteins, natural oils, silicones other than quaternary ammonium functional silicones and mixtures thereof. These compositions (with or without (J)) have been found to perform well in many personal care applications, particularly as conditioners. They are especially good conditioners where (B), a surface active agent, is more specifically a wax (natural or synthetic, such as petroleum based), a glyceryl ester (such as a stearate), a fatty alcohol (especially one having 10 to 18 carbons), another nonionic surfactant or a mixture of these.

Other more specific compositions of the present invention, also of special interest, are those comprising:

0.01 to 25, especially 0.1 to 2, weight percent (A);

1 to 40, especially 5 to 20, weight percent (B);

0.5 to 97.99, especially 30 to 92.9, weight percent (C); and 1 to 25, especially 2 to 15, weight percent (E), as well as those further comprising up to 10 weight percent of (K), a conditioning agent selected from the group consisting of cationic polymers, cationic surfactants, proteins, natural oils, silicones other than quaternary ammonium functional silicones and mixtures thereof. These compositions (with or without (K)) have been found to perform well in many personal care applications, particularly as shampoos. They are especially good shampoos where (B), a surface active agent, is more specifically a nonionic surfactant, an anionic surfactant, an amphoteric surfactant or a mixture of these.

Still other more specific compositions of the present invention, also of special interest, are those comprising:

0.01 to 25, especially 0.1 to 2, weight percent (A);

5 to 50, especially 10 to 30, weight percent (B);

0.5 to 94.89, especially 30 to 80, weight percent (C); and 0.1 to 25, especially 1 to 10, weight percent (G).

These compositions have been found to perform well in many personal care applications, particularly as moisturizers. They are especially good moisturizers where (B), a surface active agent, is more specifically a wax (natural or synthetic, such as petroleum based), a silicone polyoxyalkylene copolymer, another nonionic surfactant, an anionic surfactant or a mixture of these.

It should be understood that in this disclosure and the claims that follow that composition expressed as percent means weight percent, unless otherwise indicated specifically or clear from the context. Percentages should be understood to be based on the entire composition or entity in question.

Further, ranges stated in this disclosure and the claims that follow should be understood to disclose the entire range specifically and not just the end point(s). For example, disclosure of the range 0 to 10 should be taken to specifically disclose 2, 2.5, 3.17 and all other numbers subsumed and not just 1 and 10. Further, a disclosure of C1 to C5 (one to five carbon) hydrocarbons would be a specific disclosure of not only C1 and C5 hydrocarbons, but also of C2, C3 and C4 hydrocarbons.

It should be understood that the components of the various individual compositions of the present invention or their precursors are to be taken as distinct. In the event the description for any component on its face overlaps or includes that of another in the same composition, and no specific proviso or other indication eliminates this issue, component descriptions should be understood to contain the proviso "other than" the other component in question if the other is specific or "other than that selected for" the other component in question if the other is generic, as needed to eliminate the problem in the least restrictive way possible.

For example, as Kennan silicone quats are expected to be surface active, any surface active agent or surfactant mentioned in the same formulation as one of these quats should be taken as not being that particular quat in that formulation. Some of the components defined previously (letter designated) are actually identical; this was done for convenience when presenting claims and such components would never be paired in an individual composition or claim.

The compositions of the present invention (as well as any of the Kennan silicone quats alone) usually may be delivered in one of several forms depending on the application. These forms include "as is", diluted in a suitable diluent or as an emulsion. Given the scope of the compositions of the present invention, these forms can in some senses overlap and/or themselves be compositions according to the present invention. For example, "as is" could actually be an emulsion in some cases, and a Kennan silicone quat delivered as an emulsion may actually be, in itself, a composition according to the present invention.

The Kennan silicone quats used in the compositions of the present invention, as well as some of the compositions of the present invention themselves, are typically very viscous materials. The addition of diluents facilitates processing by reducing viscosity. Suitable diluents for this purpose include non-quaternary ammonium functional silicone fluids (especially 50 cS ($mm^2/s$) at 25 deg C. polydimethylsiloxanes), hydrocarbons (especially those having 10–24 carbons such as isododecane) and alcohols (especially those having 8 to 24 carbons and more especially those having 10 to 20 carbons such as 2-butyl octanol). It has been found that alcohols are particularly effective here, with long chain alcohols, such as 2-butyl octanol, being of special interest due to low volatility.

As previously indicated, the compositions of the present invention may be and include those in the form of emulsions (minimally containing components (A), (B) and (C) as defined above). Oil in water emulsions are frequently used, because they are generally easier to handle and disperse readily into water based formulations. It has been found that a suitable choice for (B), a surface active agent, for making emulsions is a nonionic surfactant or a mixture of nonionic surfactants. It is usually preferred that the nonionic surfactant be selected from the group consisting of alkyl ethoxylates, alcohol ethoxylates, alkylphenol ethoxylates and mixtures thereof, especially where the material selected has a hydrophilic lipophilic balance (HLB) of 2 to 20, more especially 6 to 20 and most especially 10 to 15. Cationic, amphoteric and/or anionic surfactants are generally suitable, especially if added along with a nonionic surfactant.

Some specific examples of the surfactants found to be especially useful in the preparation of the emulsions according to the present invention include a mixture of Tergitol® (TMN-6 and Tergitol® (15-S-15, a mixture of Genapol® (UD 050 and Genapol® (UD 110, a mixture of Softanol® 70 and Softanol® (120, a mixture of Lutensol® (ON70 and Lutensol® (TO5, and Lutensol® (ON70 alone. Tergitol® TMN-6 is a C12 (twelve carbon) secondary alcohol ethoxylate with an HLB of 11.7 available from the Dow Chemical Company. Tergitol® (15-S-15 is a C11–15 secondary alcohol ethoxylate with an HLB of 15.6 and is also available from the Dow Chemical Company. Genapol® (UD050 with an HLB of 11.0 and Genapol® (UD110 with an HLB of 15 are C11 oxo-alcohol polyglycol ethers available from Clariant Corporation. Softanol® (70 is a C12–14 secondary alcohol EO7 (seven ethoxy units) ethoxylate with an HLB of 12.1 available from BP Chemicals. Softanol® 120 is a C12–14 secondary alcohol EO12 (twelve ethoxy units) ethoxylate with an HLB of 14.5 also available from BP Chemicals. Lutensol® ON7 is a C13 oxo-alcohol EO7 ethoxylate with an HLB of 13.0 available from BASF. Lutensol® TO5 is a C10 oxo-alcohol EO5 ethoxylate with an HLB of 10.5 also available from BASF.

The emulsions of the present invention are typically of the "oil in water type". That is, with the silicone in a water based continuous phase. The particle sizes in such emulsions are typically 0.02 to 10 μm, with the ranges 0.02 to 2 μm and 0.02 to 0.2 μm often preferred.

Since type I, II and III Kennan silicone quats are actually subsets of the more general class, Kennan silicone quats, the compositions of the present invention include those comprising type I, II and/or III Kennan silicone quats (in particular) as the Kennan silicone quat. (The same will of course apply correspondingly to the methods and product by process defined compositions of the present invention described below.)

One method according to the present invention is a method for making a quaternary ammonium functional silicone based composition, the method comprising combining at least one member of the group consisting of Kennan silicone quat based emulsions;

Kennan silicone quats diluted in
hydrocarbons, alcohols, silicones other than quaternary ammonium functional silicones or mixtures thereof;

Kennan silicone quats; and mixtures thereof
with at least one member of the group consisting of a Kennan silicone quat, a surface active agent and water.

A further method of the present invention is a method for making a quaternary ammonium functional silicone based emulsion, the method comprising:

(1) mixing a Kennan silicone quat and at least one surface active agent, optionally diluted with water (preferably a nonionic surfactant diluted with water); and (2) combining water and at least a portion of the mixture from (1) if water is not already present therein (in the mixture from (1) that is).

The wording of the second step of this method should not be interpreted to preclude further addition of water if water is present in the mixture made in the first step.

Although not critical, it is often preferred to prepare the emulsions of the present invention at a temperature of 20 to 70 deg C.

In some instances, it is convenient to express compositions of the present invention in terms of how they were made. This is the "product by process" approach. Two such compositions of interest are as follows.

The first is a composition produced by the method comprising combining at least a Kennan silicone quat, a surface active agent and water. The second is a composition produced by the method comprising emulsifying a Kennan silicone quat with at least a surface active agent and water.

It should be understood in the first of these that "combining" means putting together in any order, and all at once or in multiple portions for each component. It should be understood in the second of these that "emulsifying" should be interpreted correspondingly.

EXAMPLES

The titles of the examples are given for convenience and should not be taken as limiting.

Example 1

Preparation of a Cationized Aminoethylaminoisobutyl Functional Silicone

An aminoethylaminoisobutyl functional silicone having a degree of polymerization (DP) of approximately 100 and containing 0.473 meq amine per gram was cationized by reaction with glycidyl trimethylammonium chloride as follows. 700.16 g of the amine functional silicone, 33.19 g of glycidyl trimethylammonium chloride (about 75 weight percent in water) and 183.08 g of isopropanol were placed in a 3 neck 2000 ml flask equipped with a stirrer, static nitrogen and a condenser. The flask was heated to reflux for four hours.

The cationized amine fluid resulting was solvent exchanged into 2-butyl octanol using the following procedure. 149.7 g of the solution of cationized amine fluid from above and 17.4 g of 2-butyl octanol were placed in a flask outfitted with a stirrer and a short path distillation head. Isopropyl alcohol was removed under reduced pressure. After cooling, some residual water was removed by adding cyclohexane and removing the water as an azeotrope. Cyclohexane was removed under reduced pressure to give the desired solution of the cationized silicone amine (a quaternary ammonium functional silicone) in 2-butyl octanol.

(It should be noted that azeotropic water removal is not absolutely required in the production of materials like those of the examples herein.)

Example 2

Preparation of Emulsions

Emulsions of silicone quaternary ammonium functional compounds were prepared according to the following overall formula:

TABLE 1

| Emulsions | |
|---|---|
| Material | Weight % |
| Solution of Quaternary Ammonium Functional Silicone prepared as in Example 1 | 20 |
| Genapol ® UD050* | 1.5–3.0 |
| Genapol ® UD110* | 3.5–7.0 |
| Water | 70–75 |

*Genapol ® UD050 (HLB = 11.0) and Genapol ® UD110 (HLB = 15) are C11 oxo-alcohol polyglycol ethers available from Clariant Corporation.

The quaternary ammonium functional silicone solution was added to a beaker followed by the Genapol surfactants. The contents of the beaker were then mixed with moderate agitation. Water was added in two portions. The first addition of water (8% of the total formulation) was followed by mixing for 30 minutes. The rest of the water was then added with mixing.

Table 2 lists the composition and properties of the specific emulsions that were used in the examples herein. All amine reactants shown (used in making the silicone quats according to the general method shown in Example 1) were trimethylsilyl terminated polydimethylsiloxanes containing amine in the form of (aminoethylaminoisobutyl) methylsiloxane units.

TABLE 2

Emulsions

| | Amine Fluid Reactant | | Quaternary Ammonium Functional Silicone Solution | | | | Emulsion Composition | | | |
|---|---|---|---|---|---|---|---|---|---|---|
| | | | | | | | Silicone | | | |
| Emulsion | Visc. (cP = mPa s) | Amine Content (meq/g) | NH Reacted (%) | Quat Type (N⁺Me₂R) R= | Quat Diluent | Quat Diluent (%) | Genapol UD050 (%) | Genapol UD110 (%) | Quat in Emulsion (%) | Particle Size (μm) |
| 1 | 2400 | 0.722 | 33 | CH₃ | Isofol ® 12¹ | 20 | 1.5 | 3.5 | 16 | 0.11 |
| 2 | 150 | 0.529 | 33 | CH₃(CH2)11 | Isofol ® 12 | 12.5 | 1.5 | 3.5 | 17.5 | 0.024 |
| 3 | 150 | 0.473 | 33 | CH₃ | Isofol ® 12 | 12.5 | 3 | 7 | 17.5 | 0.019 |
| 4 | 150 | 0.474 | 33 | CH₃ | 200 Fluid² | 50 | 3 | 7 | 10 | 0.23 |

[1] 2-butyl octanol, available from Condea Vista of Houston, TX.
[2] Dow Corning 200 ® Fluid, 50 cS (mm²/s) polydimethylsiloxane, available from Dow Corning Corp. of Midland, MI.

Example 3

Conditioners

Preparation of Conditioners

Rinse-off conditioners of the following compositions were prepared:

TABLE 3

Conditioners

| Ingredient | Conditioner A[7] (Weight %) | Conditioner B (Weight %) | Conditioner C (Weight %) |
|---|---|---|---|
| Deionized Water | q.s. to 100[8] | q.s. to 100 | q.s. to 100 |
| Hydroxyethylcellulose[1] | 1.5 | 1.5 | 1.5 |
| Cetearyl Alcohol[2] | 1.0 | 1.0 | 1.0 |
| Peg-100 Stearate & Glyceryl Stearate[3] | 1.0 | 1.0 | 1.0 |
| Emulsion 3[4] | — | 11.4[9] | — |
| Arquad 16–29[5] | — | — | 6.9[10] |
| DMDM Hydantoin Formulation[6] | 0.2 | 0.2 | 0.2 |

[1] Natrosol ® 250 MR available from Hercules of Wilmington, DE.
[2] Lanette O available from Cognis Corp. of Hoboken, NJ.
[3] Arlacel ® 165 available from Uniqema of Wilmington, DE.
[4] Emulsion 3 is from Example 2, Table 2.
[5] Arquad 16–29 is 29% active (cetrimonium chloride) and is available from Akzo Nobel Chemicals of Dobbs Ferry, NY.
[6] Glydant ®, 55% active (DMDM Hydantoin), available from Lonza, Inc. of Fairlawn, NJ.
[7] This conditioner contains no quaternary ammonium material.
[8] q.s. to 100 in this table means the addition of water to 100%.
[9] Equivalent to 2.0 weight percent of silicone quat in the conditioner.
[10] Equivalent to 2.0 weight percent of cetrimonium chloride (an organic quat) in the conditioner.

Deionized water was added to a mixing vessel and heated to 75° C. With moderate agitation, the hydroxyethyl cellulose was dispersed until fully dissolved. Heat was decreased to 60° C. and cetearyl alcohol and Peg-100 stearate & glyceryl stearate were added. Heat was then decreased to 40° C., and the emulsion of the silicone quaternary ammonium compound or the Arquad 16–29 was added, except that in conditioner A, neither was added. The conditioner was mixed for 5 to 10 minutes and then the DMDM hydantoin formulation was added. Water loss was compensated, and the formulation was mixed for an additional 5 minutes. The final pH of the conditioner formulations was approximately 6 to 7.

Preparation of Hair Samples

Slightly bleached European human hair from International Hair Importer and Products, Inc. was used for testing the conditioners prepared here. A master hand of hair about eight inches in length was subdivided into a series of individual hair tresses. Each tress weighed about 2.5 grams. A 0.5 inch (1.27 cm) section of the root end of the hair was trimmed off and the remaining hair was glued to a 2 inch by 2 inch (5.08 cm by 5.08 cm) plastic tab using DUCO CEMENT®. The cement was allowed to dry, and the hair tress was combed and trimmed to a length so that six inches (15.24 cm) of hair extended below the bottom of the plastic tab. A hole was punched in middle of tab about one fourth inch (0.635 cm) from the top. Each tress was rinsed for 15 seconds under 40° C. tap water. Using a pipette, 1.0 ml of a 9% (active) sodium lauryl sulfate solution was applied and lathered through the tress for 30 seconds. The tress was rinsed for 30 seconds under running water. Excess water was removed from the tress by passing the tress between the index and middle fingers. The tresses were placed on a tray covered with paper towels and dried overnight. Each tress was hand combed three times with the narrow teeth of an ACE® comb and had its baseline comb loading established using the INSTRON "WET" and the INSTRON "DRY" COMBING procedures.

For tests involving rinse-off conditioners, the hair tress was rinsed with tap water for 30 seconds at 40° C. The test conditioner was applied to the tress in the amount of 0.8 g, and the tress was stroked for 30 seconds. The tress was rinsed for 30 seconds under tap water at 40° C. The excess water was removed by pulling the tress through the index and middle fingers. The tresses were allowed to dry separately on a paper towel overnight at room temperature. The tresses were combed once before performing the INSTRON study.

Test Procedures

INSTRON COMBING is an industry recognized test for determining hair conditioning by the ease of wet combing and the ease of dry combing. The test employs an INSTRON strain gauge, which is equipped to measure the force required to comb the hair. Conditioning performance is based on the ability of a particular hair treatment formulation such as a shampoo or a hair conditioner to reduce the force required to comb the hair with the INSTRON strain gauge. The force is reported as Average Combing Load (ACL). The lower ACL value, the better the conditioning effect imparted by the formulation being tested. Typically, ACL baselines are initially established with "untreated" tresses that have only been washed with 9% (active) sodium lauryl sulfate solution. The effectiveness of a treatment can be expressed as the ACL of the treated tress or the percent reduction in ACL which is calculated using the formula:

$$((\text{untreated hair ACL} - \text{treated hair ACL})/\text{untreated hair ACL}) * 100.$$

According to the INSTRON WET COMBING method, the hair was first wet by dipping it in distilled water and then the hair was detangled by combing the tress three times. The tress was then retangled by dipping in distilled water three times. The excess water was removed by passing the tress through index and middle fingers twice. The tress was then placed on a hanger and INSTRON combed. The "retangle" and "INSTRON combing" steps were repeated until five data points were collected for each tress. An average combing force of three tresses was measured for each treatment. The results of the INSTRON WET COMBING test conducted with the conditioners of the present example are shown below in Table 4. Letters in the % ACL Reduction column are used to indicate that the product is superior to other designated products at a 95% confidence level. The results show that the conditioner with the silicone quaternary compound provided the largest reduction in wet combing forces compared to the control conditioner without any quaternary and the conditioner that contained only organic quaternary material, thus showing best improved conditioning of the hair.

According to the INSTRON DRY COMBING method, the hair was detangled by combing the tress 3 times. Then the hair was retangled by swirling the tress clockwise 3 times and counter clockwise 3 times. The tress was then placed on the hanger and INSTRON combed. The "retangle" and "Instron combing" steps were repeated until five data points were collected for each tress. An average combing force of three tresses was measured for each treatment. The results of the INSTRON DRY COMBING test conducted with the conditioners of the present example are shown below in Table 5. The results show that the conditioner with the silicone quaternary compound provided the largest reduction in dry combing forces compared to the control conditioner without any quaternary and the conditioner that contained only organic quaternary material, thus showing best improved conditioning of the hair.

Conditioners A and B were tested via a paired sensory comparison test for the descriptors of ease of wet combing, ease of dry combing, wet feel and dry feel of treated hair. The results are found in Table 6. A benefit with an asterisk next to it indicates statistical significance at the 95% confidence level. The sensory results also show that the conditioner with the silicone quaternary compound provided benefits of wet and dry combing and wet and dry feel over the control conditioner without quaternary material.

Conditioners A, B and C were also tested via a paired sensory comparison test for the descriptor of body/volume of treated hair. The results are found in Table 7. A benefit with an asterisk next to it indicates statistical significance at the 95% confidence level. The results show that the conditioner with the silicone quaternary compound provided an additional benefit of improved body/volume over the control conditioner without quaternary material and the conditioner that contained only organic quaternary material.

TABLE 4

INSTRON WET COMBING

| Conditioner Tested | ACL Reduction (%)[a] |
|---|---|
| A | −10 |
| B | 96 A, C |
| C | 89 A |

[a]Letter designations indicate that the conditioner tested is superior to the specified conditioners at a 95% confidence level.

TABLE 5

INSTRON DRY COMBING

| Conditioner Tested | ACL Reduction (%)[a] |
|---|---|
| A | −96 |
| B | 75 A, C |
| C | 63 A |

[a]Letter designations indicate that the conditioner tested is superior to the specified conditioners at a 95% confidence level.

TABLE 6

COMBING/FEEL SENSORY TEST

| Attribute | (A vs. B) Votes[a] |
|---|---|
| Ease of Dry Combing | 18/18 chose B* |
| Dry feel | 15/18 chose B* |
| Ease of Wet Combing | 18/18 chose B* |
| Wet Feel | 15/18 chose B* |

*Asterisk indicates that the observation is significant at the 95% confidence level.

TABLE 7

BODY/VOLUME SENSORY TEST

| Conditioners Compared | Votes[a] |
|---|---|
| A vs. B | 26/27 chose B* |
| B vs. C | 25/27 chose B* |

*Asterisk indicates that the observation is significant at the 95% confidence level.

Example 4

Conditioners

Preparation of Conditioners

Rinse-off conditioners of the following compositions were prepared:

TABLE 8

Conditioners

| Ingredient[1] | Conditioner D (Weight %) | Conditioner E (Weight %) |
|---|---|---|
| Deionized Water | q.s. to 100[3] | q.s. to 100 |
| Hydroxyethylcellulose | 1.5 | 1.5 |
| Cetearyl Alcohol | 1.0 | 1.0 |
| Peg-100 Stearate & Glyceryl Stearate | 1.0 | 1.0 |
| Silicone Quaternary Formulation[2] | — | 2.0[4] |
| DMDM Hydantoin Formulation | 0.2 | 0.2 |

[1]Notes 1, 2, 3 and 6 from Table 3 apply.
[2]From Example 1.
[3]q.s. to 100 in this table means the addition of water to 100%.
[4]Equivalent to 1.7 weight percent silicone quat in the conditioner.

Testing

INSTRON combing tests were performed as in Example 3 using the conditioners of the present example. The results in Tables 9 and 10 show that the conditioner with silicone quaternary compound provided a large reduction in wet and dry combing forces unlike the control conditioner without silicone quaternary material, thus demonstrating conditioning improvement due to the silicone quaternary material.

TABLE 9

INSTRON WET COMBING

| Conditioner Tested | ACL Reduction (%)[a] |
|---|---|
| D | −22 |
| E | 87 D |

[a]Letter designations indicate that the conditioner tested is superior to the specified conditioners at a 95% confidence level.

TABLE 10

INSTRON DRY COMBING

| Conditioner Tested | ACL Reduction (%)[a] |
|---|---|
| D | −14 |
| E | 50 D |

[a]Letter designations indicate that the conditioner tested is superior to the specified conditioners at a 95% confidence level.

Example 5

Conditioners

Preparation of Conditioners

Rinse-off conditioners of the following compositions were prepared:

TABLE 11

| | Conditioners | | | |
|---|---|---|---|---|
| Ingredient[1] | Conditioner F (Weight %) | Conditioner G (Weight %) | Conditioner H (Weight %) | Conditioner I (Weight %) |
| Deionized Water | q.s. to 100[3] | q.s. to 100 | q.s. to 100 | q.s. to 100 |
| Hydroxyethlcellulose | 1.5 | 1.5 | 1.5 | 1.5 |
| Cetearyl Alcohol | 1.0 | 1.0 | 1.0 | 1.0 |
| Peg-100 Sterate & Glyceryl Stearate | 1.0 | 1.0 | 1.0 | 1.0 |
| Emulsion 3[2] | 11.4[4] | — | — | — |
| Emulsion 4[2] | — | 20.0[4] | — | — |
| Emulsion 2[2] | — | — | 11.4[4] | — |
| Emulsion 1[2] | — | — | — | 12.5[4] |
| DMDM Hydantoin Formulation | 0.2 | 0.2 | 0.2 | 0.2 |

[1]Notes 1, 2, 3 and 6 from Table 3 apply.
[2]These are emulsions from Example 2, Table 2.
[3]q.s. to 100 in this table means the addition of water to 100%.
[4]Equivalent to 2.0 weight percent silicone quat in the respective conditioners.

Testing

INSTRON combing testing was done as in Example 3 using the conditioners of the present example. Results in Tables 12 and 13 show that all of the conditioners with the silicone quaternary compounds tested provided a reduction in wet and dry combing forces, and thus resulted in improved condition of the hair.

TABLE 12

INSTRON WET COMBING

| Conditioner Tested | ACL Reduction (%)[a] |
|---|---|
| F | 96 H, I |
| G | 95 H, I |
| H | 91 |
| I | 90 |

[a]Letter designations indicate that the conditioner tested is superior to the specified conditioners at a 95% confidence level.

TABLE 13

INSTRON DRY COMBING

| Conditioner Tested | ACL Reduction (%)[a] |
|---|---|
| F | 64 H |
| G | 61 H |
| H | 54 |
| I | 71 F, G, H |

[a]Letter designations indicate that the conditioner tested is superior to the specified conditioners at a 95% confidence level.

Example 6

Conditioners

Preparation of Conditioners

Rinse-off conditioners of the following compositions were prepared:

TABLE 14

| | Conditioners | | | | |
|---|---|---|---|---|---|
| Ingredient[1] | Conditioner J (Weight %) | Conditioner K (Weight %) | Conditioner L (Weight %) | Conditioner M (Weight %) | Conditioner N (Weight %) |
| Deionized Water | q.s. to 100[3] | q.s. to 100 | q.s. to 100 | q.s. to 100 | q.s to 100 |
| Hydroxyethlcellulose | 1.5 | 1.5 | 1.5 | 1.5 | 1.5 |
| Cetearyl Alcohol | 1.0 | 1.0 | 1.0 | 1.0 | 1.0 |
| Peg-100 Sterate & Glyceryl Stearate | 1.0 | 1.0 | 1.0 | 1.0 | 1.0 |
| Emulsion 3[2] | 11.4 | 5.7 | 2.86 | 1.43 | 0.57 |
| DMDM Hydantoin Formulation | 0.2 | 0.2 | 0.2 | 0.2 | 0.2 |

[1]Notes 1, 2, 3 and 6 from Table 3 apply.
[2]These are emulsions from Example 2, Table 2; Equivalent weight percents of silicone quaternary in conditioner J, K, L, M, N are 2.0, 1.0, 0.5, 0.25 and 0.10, respectively.
[3]q.s. to 100 in this table means the addition of water to 100%.

Testing

INSTRON combing was done as in Example 3 using the conditioners of the present example. Results in Tables 15 and 16 show that the silicone quaternary compound tested at concentrations as low as 0.1% in the rinse-off conditioner formulation still provided a reduction in wet and dry combing forces, and thus improved the condition of the hair.

TABLE 15

INSTRON WET COMBING

| Conditioner Tested | ACL Reduction (%)[a] |
|---|---|
| J | 96 M, N |
| K | 96 L, M, N |
| L | 94 N |
| M | 88 N |
| N | 45 |

[a]Letter designations indicate that the conditioner tested is superior to the specified conditioners at a 95% confidence level.

TABLE 16

INSTRON DRY COMBING

| Conditioner Tested | ACL Reduction (%)[a] |
|---|---|
| J | 68 N |
| K | 69 N |
| L | 67 N |
| M | 69 N |
| N | 33 |

[a]Letter designations indicate that the conditioner tested is superior to the specified conditioners at a 95% confidence level.

Example 7

Shampoos

Preparation of Shampoos

Conditioning shampoos of the following compositions were prepared:

TABLE 17

Shampoos

| Ingredient | Shampoo A (Weight %) | Shampoo B (Weight %) |
|---|---|---|
| Deionized Water | q.s. to 100[7] | q.s. to 100 |
| Sodium Laureth Sulfate Formulation[1] | 30 | 30 |
| Cocamide DEA[2] | 3.0 | 3.0 |
| PEG-150 Pentaerythrityl Tetrastearate[3] | 1.5 | 1.5 |
| Cocamidopropyl Betaine Formulation[4] | 7.0 | 7.0 |
| Emulsion 4[5] | — | 11.4[8] |
| DMDM Hydantoin Formulation[6] | 0.2 | 0.2 |

[1]Standapol ES-3, 30% active (sodium laureth sulfate), available from Cognis Corp. of Hoboken, NJ.
[2]Calamide C available from Pilot Chemical Corp. of Santa Fe Springs, CA.
[3]Crothix available from Croda, Inc. of Parsippany, NJ.
[4]Monateric CAB, 30% active (cocamidopropyl betaine), available from Uniqema of Paterson, NJ.
[5]This is from Example 2, Table 2.
[6]Glydant ®, 55% active (DMDM Hydantoin), available from Lonza, Inc. of Fairlawn, NJ.
[7]q.s. to 100 in this table means the addition of water to 100%.
[8]Equivalent to 2.0 weight percent silicone quaternary in the shampoo.

Deionized water was added to a mixing vessel and heated to 65° C. With moderate agitation, the PEG-150 pentaerythrityl tetrastearate was completely dispersed. The heat was turned off and the sodium laureth sulfate formulation, Cocamide DEA, and the cocamidopropyl betaine formulation were added. When the temperature was less than 40° C., the silicone emulsion was added (in the case of shampoo B). The shampoo was mixed for 5 to 10 minutes and then the DMDM hydantoin formulation was added. Water loss was compensated, and the formulation was mixed for an additional 5 minutes. The final pH of the shampoo formulations was approximately 6 to 7.

Testing

INSTRON WET COMBING testing was conducted as in Example 3 with the shampoos of the present example. Results are shown below in Table 18. The results show that the shampoo with the silicone quaternary compound provided a reduction in wet combing forces unlike the control shampoo without silicone quaternary, and thus improved conditioning.

Hair tresses treated with shampoos A and B were also subjected to a paired sensory comparison test for the descriptor of ease of wet combing. The results are found in Table 19. The sensory results also show that the shampoo with the silicone quaternary compound provided a wet combing benefit over the control shampoo without silicone quaternary.

TABLE 18

INSTRON WET COMBING

| Conditioning Shampoo Tested | ACL Reduction (%)[a] |
|---|---|
| A | −12 |
| B | 15 A |

[a]Letter designations indicate that the shampoo tested is superior to the specified shampoo(s) at a 95% confidence level.

TABLE 19

Wet Combing Sensory Test (A vs. B)

| Attribute | Votes[a] |
|---|---|
| Ease of Wet Combing | 13/18 chose B* |

[a]Asterisk indicates that the observation is significant at the 95% confidence level.

Example 8

Shampoos

Preparation of Shampoos

Conditioning shampoos of the following compositions were prepared:

TABLE 20

Shampoos

| Ingredient[1] | Shampoo C (Weight %) | Shampoo D (Weight %) |
|---|---|---|
| Deionized Water | q.s. to 100[3] | q.s. to 100 |
| Sodium Laureth Sulfate Formulation | 30 | 30 |
| Cocamide DEA | 3.0 | 3.0 |
| PEG-150 Pentaerythrityl Tetrastearate | 1.5 | 1.5 |
| Cocamidopropyl Betaine Formulation | 7.0 | 7.0 |
| Silicone Quaternary Formulation[2] | — | 2.0[4] |
| DMDM Hydantoin Formulation | 0.2 | 0.2 |

[1]1, 2, 3, 4 and 6 from Table 17 apply.
[2]From Example 1.
[3]q.s. to 100 in this table means the addition of water to 100%.
[4]Equivalent to 1.7 weight percent silicon quat in the shampoo.

Testing

INSTRON TESTING was done as in Example 3 using the shampoos of the present example. The results in Tables 21 and 22 show that the shampoo with silicone quaternary compound provided a reduction in wet and dry combing forces, unlike the control shampoo without silicone quaternary material, and thus improved conditioning.

TABLE 21

INSTRON WET COMBING

| Conditioning Shampoo Tested | ACL Reduction (%)[a] |
|---|---|
| C | −29 |
| D | 16 C |

[a]Letter designation indicates that the shampoo tested is superior to the specified shampoo at an 85% confidence level.

TABLE 22

INSTRON DRY COMBING

| Conditioning Shampoo Tested | ACL Reduction (%)[a] |
|---|---|
| C | −14 |
| D | 31 C |

[a]Letter designation indicates that the shampoo tested is superior to the specified shampoo(s) at an 95% confidence level.

Example 9

Moisturizers

Preparation of Moisturizers

Skin care moisturizers of the following compositions were prepared:

TABLE 23

Moisturizers

| Ingredient | Moisturizer A (Weight %) | Moisturizer B (Weight %) |
|---|---|---|
| Phase A | | |
| Cyclopentasiloxane[1] | 10 | 10 |
| Cyclomethicone and Dimethicone Copolyol[2] | 10 | 10 |
| Phase B | | |
| Deionized Water | q.s. to 100[5] | q.s. to 100 |
| Glycerin[3] | 5.0 | 5.0 |
| Emulsion 3[4] | — | 11.4[6] |

[1]Dow Corning ® 245 Fluid, available from Dow Corning, Midland, MI.
[2]Dow Corning ® 5225C Formulation Aid, available from Dow Corning, Midland, MI.
[3]Available from Fisher of Fair Lawn, NJ.
[4]From Example 2, Table 2.
[5]q.s. to 100 in this table means the addition of water to 100%.
[6]Equivalent to 2.0 weight percent silicone quaternary in the moisturizer.

The ingredients in Phase A were combined and mixed until uniform using a dual-blade, turbulent-style mixing action. The ingredients in Phase B were combined and mixed until uniform. The mixing speed of Phase A was increased to a tip velocity of 900 ft/min and Phase B was added very slowly (over 10 minutes) to it. Mixing was continued for an additional 10 minutes.

Testing

Sensory testing for skin feel attributes was performed using moisturizers A and B according to ASTM Standards E 1958–98 (Standard Guide for Sensory Claim Substantiation) and E 253 (Terminology Relating to Sensory Evaluation of Materials and Products), as well as ISO Standard 6658 (Sensory Analysis—Methodology—General Guidance). The results are found in Table 24. Higher scores indicate a greater degree of skin slipperiness. The results show that the formulation containing the silicone quaternary compound (Moisturizer B) provided a benefit of improved slipperiness over the control formulation (Moisturizer A) without the silicone quaternary material.

TABLE 24

SKIN SLIPPERINESS SENSORY TEST

| Moisturizer | Score |
|---|---|
| A | 5.1 |
| B | 6.2* |

*The difference in slipperiness between moisturizer A and B is significant at the 95% confidence level.

Example 10

Fabric Softeners

Preparation of Fabric Softeners

Rinse-cycle fabric softener formulations of the following compositions were prepared:

TABLE 25

| Ingredient | Softener A (Weight %) | Softener B (Weight %) |
|---|---|---|
| Dihydrogenated Tallowethyl Hydroxyethylmonium Methosulfate (DTHM)[1] | 100 | 85.4 |
| Emulsion 2[2] | — | 14.6 |

[1]Tetranyl L1/90, 16% active (DTHM), available from KAO Chemicals Europe of Barcelona Spain.
[2]From Example 2, Table 2.

A standard fabric softener formulation was provided by KAO Corporation (Softener A). To this formulation, the silicone emulsion was added using moderate agitation to obtain a homogeneous mixture (Softener B).

Testing

Performance of the materials was evaluated using protocols that would closely reproduce consumer habits while attempting to reduce variability in test conditions. Four characteristics were evaluated, WRINKLE REDUCTION, EASE OF IRON, WRINKLE REMOVAL, and SOFTNESS. All testing was conducted using a 16-member panel. Testing was performed using identically desized fabric treated with the reference softener formulation A or the reference softener with the silicone quaternary ammonium emulsion added (softener formulation B). For the ease of ironing, wrinkle reduction, and wrinkle removal tests, 100% cotton pillowcases were used. For the softness test, 100% cotton terry towels were used.

For all tests, the treatment procedure consisted of combining 16 pillowcases and 1 terry towel per ballast. Each ballast was washed in a Miele® Novotronic 1918 front-loading washing machines using a standard wash setting with a wash water temperature setting of 40° C. (105° F.). Each ballast was washed using 66 grams of Tides® HE powdered laundry detergent. The wash cycle water used was treated soft water. The fabric softener formulation wash placed in the machine reservoir designated for the dispensing of the softener. Thirty-five grams of softener formulation was dispensed during the final rinse of the machine cycle. During the dispensing of the fabric softener, an aliquot of premixed hard water, which would increase the rinse hardness to 90 ppm, was added followed by an additional 100 ml of deionized water to flush the dispensing unit. The wash cycle was allowed to proceed automatically through the final spin cycle. Once the wash and rinse cycles were completed, the ballast was removed, shaken once to remove gross wrinkles and each pillow case and towel were hung individually by two corners with the fabric length in the vertical position using clips to secure one end to a clothes hanger to dry. Ballasts were then dried in a controlled humidity environment (22° C., less than 65% relative humidity) and tested after 24 hours.

The WRINKLE REDCUTION tests were conducted in accordance with AATCC test method 124-1996 "Appearance of Fabrics after Repeated Home Laundering". This method was developed to evaluate the smoothness of flat fabric specimens after repeated laundering. Each panelist was presented with two pillowcases as above displayed on a vertical panel painted gray. The panelists were asked to choose the less wrinkled pillowcase. A paired comparison evaluation of the results was statistically processed to determine their level of significance. Binomial distribution statistics were used to determine the least significant difference at various confidence levels between the fabric treated with the reference and the fabric treated with the reference and silicone quaternary sample. Results of the WRINKLE REDUCTION test can be seen in Table 26.

The EASE OF IRON test was completed using the pillowcases from the WRINKLE REDUCTION test. Panelists were presented the pillowcases on an ironing board in a consistent manner. Panelists were instructed to iron one side of the pillowcase and observe how easily the iron glided across the fabric surface as well as the ease of wrinkle removal. The iron was allowed to recover in temperature between each completed pillowcase. Panelists were asked questions regarding EASE OF IRONING and the results are noted in Table 26.

Further WRINKLE REDUCTION tests were completed by presenting the ironed pillowcases in a similar fashion to that of the earlier WRINKLE REDUCTION evaluations. The panelists were again asked similar questions to those in previous evaluations. The results of the evaluation are listed in Table 26.

SOFTNESS evaluations were completed using the single terry towel from each ballast. Panelists were presented towels, each treated with a different treatment. Each panelist then felt each pillowcase and determined which was softer. The results of the evaluation are listed in Table 26.

TABLE 26

| Attribute | Votes (A vs. B) | Confidence Level |
|---|---|---|
| Wrinkle Reduction | 10/16 Chose B | 90% |
| Ease of Ironing | 12/16 Chose B | 99% |
| Wrinkle Removal | 11/16 Chose B | 95% |
| Softness | 10/16 Chose B | 90% |

Specific embodiments previously described should be taken as illustrative and not as limiting the claims that follow unless specifically indicated.

What is claimed is:

1. A quaternary ammonium functional silicone based composition comprising:

(A) a silicone having the formula:

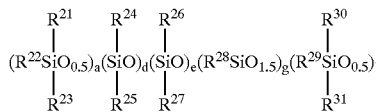

where $R^{21}$, $R^{22}$, $R^{23}$, $R^{30}$ and $R^{31}$ are independently hydroxy, phenoxy, alkoxy or monovalent hydrocarbon groups having 1–20 carbon atoms;

$R^{24}$, $R^{25}$ and $R^{27}$ are independently monovalent hydrocarbon groups having 1–20 carbon atoms;

$R^{28}$ is a monovalent hydrocarbon group having 1–20 carbon atoms, or contains nitrogen and may at least in part represent a group or groups of the form —$R^1$—Z—$Q^3$;

$R^{26}$ and $R^{29}$ contain nitrogen and where present represent, at least in part, a group or groups of the form —$R^1$—Z—$Q^3$;

—$R^1$— is either a divalent hydrocarbon group having 1–20 carbon atoms, that may optionally incorporate ether or ester functionality, or —$R^{17}$N($Q^1$)$R^{18}$—;

—$R^{17}$— and —$R^{18}$— are independently divalent hydrocarbon groups having 1–20 carbon atoms that may optionally incorporate ether or ester functionality;

—$Q^1$ is —$CH_2CH(OH)CH_2N^+(R^4)(R^5)(R^6)$ $X^-$, hydrogen or a monovalent hydrocarbon group having 1–20 carbon atoms that may optionally incorporate hydroxy, diol, amide, ether or ester functionality;

$R^4$, $R^5$ and $R^6$ are independently monovalent hydrocarbon groups having 1–20 carbon atoms;

$X^-$ is a counter ion;

—Z— is —N($Q^2$)—;

—$Q^3$ and —$Q^2$ are independently —$CH_2CH(OH)CH_2N^+(R^4)(R^5)(R^6)$ $X^-$, hydrogen or a monovalent hydrocarbon group having 1–20 carbon atoms that may optionally incorporate hydroxy, diol, amide, ether or ester functionality;

a, b, d, e and g are all greater than or equal to zero;

a=0 to 2+g;

b=0 to 2+g;

d=0 to 500;

e=0 to 100;

g=0 to 100;

a+b is greater than or equal to 2; and e+b>0, with the proviso that at least a portion of $Q^1$, $Q^2$, and $Q^3$ present in the composition is —$CH_2CH(OH)CH_2N^+(R^4)(R^5)(R^6)$ $X^-$;

(B) a surface active agent; and (C) water.

2. The composition of claim 1 wherein (B) is selected from the group consisting of glyceryl esters, fatty alcohols, nonionic surfactants and mixtures thereof.

3. The composition of claim 2 further comprising (D) a conditioning agent selected from the group consisting of cationic polymers, cationic surfactants, proteins, natural oils, silicones other than quaternary ammonium functional silicones, a hydrocarbon other than a wax, an anionic surfactant, an amphoteric surfactant and mixtures thereof.

4. The composition of claim 1 wherein (B) is selected from the group consisting of nonionic surfactants, anionic surfactants, amphoteric surfactants and mixtures thereof.

5. The composition of claim 4 further comprising (E), a cosurfactant selected from the group consisting of betaines, monoalkyl alkanolamides, dialkyl alkanolamides, amine oxides, amine glycinates, amine propionates, amine sultaines and mixtures thereof, with the proviso that the specific materials selected for (B) and (E) be distinct.

6. The composition of claim 5 further comprising (F) a conditioning agent selected from the group consisting of cationic polymers, cationic surfactants, proteins, waxes, natural oils, silicones other than quaternary ammonium functional silicones, a hydrocarbon other than a wax and a mixtures thereof.

7. The composition of claim 1 further comprising (G) a polyhydric alcohol, and wherein component (B) is selected from the group consisting of silicone polyoxyalkylene copolymers, nonionic surfactants, anionic surfactants and mixtures thereof, with the proviso that the specific materials selected for (B) and (G) are distinct.

8. The composition of claim 7 further comprising (H) a material selected from the group consisting of a hydrocarbon other than a wax, a natural oil, a cationic surfactant, an amphoteric surfactant and mixtures thereof.

9. The composition of claim 8 further comprising (J) a conditioning agent selected from the group consisting of cationic polymers, cationic surfactants, proteins, natural oils, silicones other than quaternary ammonium functional silicones and mixtures thereof.

* * * * *